US007531301B2

(12) United States Patent
Hu et al.

(10) Patent No.: US 7,531,301 B2
(45) Date of Patent: *May 12, 2009

(54) SYSTEMS AND METHODS FOR IDENTIFYING ORGAN TRANSPLANT RISK

(75) Inventors: Huaizhong Hu, Madison, WI (US); Alice Puchalaki, Madison, WI (US)

(73) Assignee: Renovar, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/879,442

(22) Filed: Jul. 17, 2007

(65) Prior Publication Data

US 2007/0287188 A1 Dec. 13, 2007

Related U.S. Application Data

(63) Continuation of application No. 10/313,807, filed on Dec. 6, 2002, now Pat. No. 7,244,555.

(60) Provisional application No. 60/380,569, filed on May 14, 2002.

(51) Int. Cl.
*C12Q 1/00* (2006.01)

(52) U.S. Cl. ......................................................... 435/4

(58) Field of Classification Search ........................ None
See application file for complete search history.

(56) References Cited

U.S. PATENT DOCUMENTS

| 5,484,707 | A | 1/1996 | Goldblum et al. | |
|---|---|---|---|---|
| 2003/0215886 | A1 | 11/2003 | Hu | |
| 2005/0112688 | A1 | 5/2005 | Hu | |
| 2005/0158801 | A1 | 7/2005 | Hu | |
| 2006/0084184 | A1* | 4/2006 | Hu et al. ..................... | 436/174 |
| 2007/0134728 | A1* | 6/2007 | Hu et al. ..................... | 435/7.1 |

FOREIGN PATENT DOCUMENTS

| WO | 200178708 | 10/2001 |
|---|---|---|
| WO | 2003098185 | 11/2003 |
| WO | 2003098185 ISR | 11/2003 |
| WO | 2005012907 | 1/2005 |
| WO | 2005002416 | 10/2005 |

OTHER PUBLICATIONS

U.S. Appl. No. 10/903,797, filed May 26, 2005 by Huaizhong Hu, et al.
U.S. Appl. No. 10/313,807, filed Feb. 6, 2002 by Huaizhong Hu, et al.
Moreb Jans S, et al, "Monitoring serum and urine osteoprotegrin levens during the treatment of patients with multiple myeloma," Blood, Nov. 16, 2003, p. 374b, Ann Meeting of the American Society of Hematology; vol. 102 No. 11, San Diego CA USA.
Zhu H, Snyder M; "Protein chip technology," Current Opinion in Chemical Biology, 2003 vol. 7, pp. 55-63.
Cutler P, "Protein arrays: The current state of the art," Proteomics, 2003 vol. 3, pp. 3-18.
Koehler, "Continuous culture of fused cells secreting antibody of predefined specificity," Nature, 1975, vol. 256, p. 495.
Hu et al. "Elevation of CXCR3-Binding Chemokines in Urine Indicates Acute Renal-Allograft Dysfunction," American J. Transol. 2004'4:432-437.
Segerer et al. "Chemokines, Chemokine Receptors, and Renal Disease: From Basic Science To Pathophysiologic and Therapeutic Studies," J. Am. Soc. Nephrol. 2000, 11:152-176'.
Nelson et al. "Chemokines, Chemokine Receptors, and Allograft Rejection," Immunity. 2001, 14:377-386 April.
Romagnani et al. "Role for Interactions Between IP-10/Mig and CXCR2 in Proliferative Glomerulonephritis," J Am Soc Nephrol. Dec. 10, 1999(12):2518•26.
Gao et al. Transplantation. Oct. 15, 2001:72(7): 1199•205.
Raybiotech. Inc. RayBio Cytokine Antibody Array web based product literature.
Upstate Cell Signaling Solutions, Beadlyte, Kits and Reagents for Luminex, Detection Systems web based product literature Kils.
Hancock et al. J Exp Med. Nov. 20, 2000; 192(10):IS 15-20.
Gerard et al. Nat Immunol. Feb. 2, 2001(2): 108•15.
Wong et al. Curr Opin Nephrol Hypertens. Nov. 10, 2001(6):807-11 (abstract only).
Maier et al. Shock. Aug. 14, 2000(2): 187•92 (abstract only).
Poppas et al., Urology Aug. 1998 52(2): 268-75; discussion 275-6 (abstract only).
Rovin et al. Am J Kidney Dis. 1996 Mav-27(5):640-6 (abstract only).
Olszyna et al J Clin Immunol. Nov. 19, 1999(6):399-405 (abstract only).
Kacprzyk, Pol Arch Med Wewn, Sep. 2000:108(3):837-42 (abstract only).
Sibbring: et at "Localization for C-X-C chemokines to renal tubular epithelial cells in human kidney transplants is not confined to acute cellular rejection," Transpl Immunol. Dec. 6, 1998(4):203-8 (Abstract Only).
Pattison et at Lancet. Jan. 22, 1994: 343(8891):209-11 (abstract only).
Segerer et at Kidney Dis Int. Jul. 1999•56(1) 52•64 (abstract only).
Grandaliano et al. Transplantation. Feb. 15, 1997: 63(3):414-20 (abstract only).
Yun et al. Transplantation. Jun. 27, 2000•69(12):2515•24 (abstract only).
Segerer et al. Am. J. Kidney Dis. Mar. 2001 37:518-31.
Hancock J. Am Soc. Nephrol. Mar. 13, 2002:821-824.
Afrouzian et al. J. Soc. Nephrol. Mar. 13, 2002:1199-1209.
Romagnani et al., "High expression of chemokines intereron-gamma Inducible protein of 10kDa(IP-10), Monokines induced by interferon-y (MIG) and of their receptor (CXCR3) in acute renal rejection" Am J Transplant, vol. S343, Abstract #825 (2001).
Inston et al., "The revolving role of chemokines and their receptors in acute allograft rejection,"Nephrol Dial Transplant (2002) 17:1374-1379.

(Continued)

*Primary Examiner*—Cecilia Tsang
*Assistant Examiner*—Amanda P Wood
(74) *Attorney, Agent, or Firm*—Casimir Jones, S.C.

(57) ABSTRACT

The present invention relates to methods of diagnosing and predicting organ transplant rejection. In particular, the present invention relates to the detection and prediction of kidney transplant rejection by detection of CXCR3 and CCL chemokines in urine. The present invention provides improved methods of diagnosing organ rejection and determining the efficacy of anti-rejection drugs.

4 Claims, 1 Drawing Sheet

OTHER PUBLICATIONS

Loetscher et al., "Chemokine Receptor Specific for IP10 and Mig: Structure, Function, and Expression in Activated T-Lymphocytes," J Exp Med vol. 184 Sep. 1996, 963-969.

Wada et al., "Chemokines: New Target Molecules in Renal Diseases," Clinical and Experimental Nephrology 4 (4):273, 2000 (Abstract Only).

Schindler et al., "Renal Problems after lung transplantation of cystic fibrosis patients," Nephrol Dial Transplant, (2001) V. 16, pp. 1324-1338.

Sanchez et al., "Preoperative and perioperative predictors of the need for renal replacement therapy after orthotopic liver transplantation," Transplantation, (Oct. 25, 2004) vol. 7, No. 7, pp. 1048-1054.

* cited by examiner

SYSTEMS AND METHODS FOR IDENTIFYING ORGAN TRANSPLANT RISK

This application is a continuation of U.S. patent application Ser. No. 10/313,807, filed Dec. 6, 2002, now U.S. Pat. No. 7,244,555, issued Jul. 17, 2007, which claims priority to U.S. provisional patent application Ser. No. 60/380,569 filed on May 14, 2002, both of which are incorporated herein by reference.

FIELD OF THE INVENTION

The present invention relates to methods of diagnosing and predicting organ transplant rejection. In particular, the present invention relates to the detection and prediction of kidney transplant rejection by detection of CXCR3 and CCL chemokines in urine. The present invention further relates to methods and compositions for assessing the efficacy of anti-rejection agents.

BACKGROUND OF THE INVENTION

Approximately 12,000 kidney transplants are performed annually in the United States. Despite the availability of potent immunosuppressive agents, graft rejection remains the main complication of renal transplantation. For example, approximately 50% of all renal allograft recipients are thought to suffer at least one episode of graft rejection. The likelihood of kidney loss due to rejection is highest during the first year post transplant (10-20%), but a small proportion (3-5%) of kidneys are rejected each year even after the first year.

Statistics indicate that graft rejection is often not detected early enough in the rejection episode to allow initiation of countervailing treatment in time to prevent the organ rejection with immunosuppressive agents at a time when the rejection process could be effectively halted and/or prevented altogether.

The diagnosis of acute allograft rejection is classically based on the presence of one or more symptoms. For example, symptoms of acute allograft rejection include weight gain, reduced urine output, increased serum creatine concentrations, hypertension, fever, and graft enlargement and tenderness. However, the use of these symptoms alone to detect rejection is not adequate. Currently, most transplant rejection episodes are detected by periodically measuring the function of the transplanted kidney, for example by using biochemical tests such as assays that measure serum creatine concentrations.

Presently, renal biopsy remains the most definitive test to specifically diagnose renal allograft rejection. However, this method has major limitations. For example, since the biopsy procedure itself has complications, and since a portion of the renal transplant is removed during each biopsy, transplant biopsy cannot be performed on a routine or even frequent basis to monitor renal allograft rejection. In addition, the invasive nature of a renal biopsy is both uncomfortable and inconvenient for patient subjects. Accurate interpretation of the renal transplant biopsy also demands the expertise of a pathologist with extensive experience in analyzing a biopsy sample for evidence of renal transplant rejection. Hence, renal biopsies are reserved for those patients that demonstrate other clinical and/or laboratory evidence of renal allograft rejection, thus limiting its use or potential use in detecting early graft rejection.

A method for the early detection and/or prediction of graft rejection would thus be an important clinical tool for maintaining the viability of a transplanted organ.

SUMMARY OF THE INVENTION

The present invention relates to methods of diagnosing and predicting organ transplant rejection. In particular, the present invention relates to the detection and prediction of kidney transplant rejection by detection of CXCR3 and CCL chemokines in urine.

Accordingly, in some embodiments, the present invention provides a method of detecting rejection markers, comprising providing a urine sample from a subject, wherein said subject has undergone organ transplant; reagents for detection of a CXCR3 ligand or CCR-5 receptor ligand (e.g., CCL chemokines); and detecting the presence of said ligand in said urine sample using said reagents. In some embodiments, the method further provides the step of predicting transplant rejection risk in the subject based on the result of the detecting. In other embodiments, the method further provides the step of detecting transplant rejection risk in the subject based on the result of the detecting. The present invention is not limited to the detection of rejection markers associated with transplant of a particular organ. Indeed, the methods of the present invention are applicable to the detection of rejection markers for any organ transplant (e.g., kidney organ transplant). In some embodiments, detecting the presence of the ligand in the urine sample comprises detecting the amount of the ligand in the urine sample. The present invention is not limited to the detection of a particular ligand. Any suitable ligand is contemplated including, but not limited to, IP-10, MIG, I-TAC, MIP-1α, MIP-3α, and MIP-1β. In some embodiments, the ligand is a full length ligand. In other embodiments, the ligand is a fragment of the full length ligand. In some embodiments, the reagents comprise reagents for performing an immunoassay. The present invention is not limited to a particular immunoassay. Any suitable immunoassay is contemplated including, but not limited to, ELISA, radioimmunoassay, automated immunoassay, cytometric bead assay, and immunoprecipitation assay. In some embodiments, the ELISA is a quantitative ELISA assay. In some embodiments, the present invention further comprises the step of determining a treatment course of action based on the predicting kidney transplant rejection risk. In some embodiments, the treatment course of action comprises the administration of anti-rejection therapy. In other embodiments, the treatment course of action comprises continued monitoring. In some embodiments, the present invention further comprises the step of determining the presence or absence of a concurrent infection in the subject. In some embodiments, the determining comprises determining the body temperature of the subject. In other embodiments, the determining comprises the detection of a bacterial infection in the subject. In still further embodiments, the determining comprises the detection of a viral infection in the subject.

The present invention further provides a method of diagnosing transplant rejection in a subject, comprising providing a urine sample from a subject, wherein the subject has undergone organ transplant; reagents for detection of a CXCR3 ligand or CCR-5 receptor ligand (e.g., CCL chemokines); and detecting the presence of the ligand in the urine sample using the reagents; and diagnosing transplant rejection in the subject based on the result of the detecting. In some embodiments, detecting the presence of the ligand in the urine sample comprises detecting the amount of the ligand in the urine sample. The present invention is not limited to the detection of rejection markers associated with transplant of a particular organ. Indeed, the methods of the present invention are applicable to the detection of rejection markers for any organ transplant (e.g., kidney organ transplant). The present invention is not limited to the detection of a particular ligand. Any suitable ligand is contemplated including, but not limited to, IP-10, MIG, I-TAC, MIP-1α, MIP-3α, and MIP-1β. In some embodiments, the ligand is a full-length ligand. In other embodiments, the ligand is a fragment of the full length ligand. In some embodiments, the reagents comprise reagents for performing an immunoassay. The present invention is not limited to a particular immunoassay. Any suitable immunoassay is contemplated including, but not limited to, ELISA, radioimmunoassay, automated immunoassay, and immunoprecipitation assay. In some embodiments, the ELISA is a quantitative ELISA assay. In some embodiments, the method further comprises the step of determining a treatment course of action based on the diagnosing kidney transplant rejection. In some embodiments, the treatment course of action comprises the administration of anti-rejection therapy. In other embodiments, the treatment course of action comprises the administration of more aggressive anti-rejection therapy. In some embodiments, the method further comprises the step of determining the presence or absence of a concurrent infection in the subject. In some embodiments, determining comprises determining the body temperature of the subject. In other embodiments, the determining comprises the detection of a bacterial infection in the subject. In still further embodiments, the determining comprises the detection of a viral infection in the subject.

The present invention additionally provides a method of determining a treatment course of action, comprising providing a urine sample from a subject, wherein the subject has undergone organ transplant reagents for detection of a rejection polypeptide; and detecting the amount of the rejection polypeptide in the urine sample using the reagents; and determining a treatment course of action based on the detecting. In some embodiments, the treatment course of action comprises the administration of anti-rejection therapy. In other embodiments, the treatment course of action comprises the administration of more aggressive anti-rejection therapy. In still further embodiments, the treatment course of action comprises continued monitoring. The present invention is not limited to the detection of rejection markers associated with transplant of a particular organ. Indeed, the methods of the present invention are applicable to the detection of rejection markers for any organ transplant (e.g., kidney organ transplant). In some embodiments, the rejection polypeptide comprises a chemokine. In some embodiments, the chemokine comprises a CXCR3 ligand or a CCL chemokine. The present invention is not limited to the detection of a particular ligand. Any suitable ligand is contemplated including, but not limited to, IP-10, MIG, I-TAC, MIP-1α, MIP-3α, and MIP-1β. The present invention is not limited to the detection of a particular ligand. Any suitable ligand is contemplated including, but not limited to, IP-10, MIG, I-TAC, MIP-1α, MIP-3α, and MIP-1β. In some embodiments, the ligand is a full-length ligand. In other embodiments, the ligand is a fragment of a full-length ligand. In some embodiments, the reagents comprise reagents for performing an immunoassay. The present invention is not limited to a particular immunoassay. Any suitable immunoassay is contemplated including, but not limited to, ELISA, radioimmunoassay, automated immunoassay, and immunoprecipitation assay. In some embodiments, the ELISA is a quantitative ELISA assay. In some embodiments, the method further comprises the step of determining the presence or absence of a concurrent infection in the subject. In some embodiments, the determining comprises determining the body temperature of the subject. In other embodiments, the determining comprises the detection of a bacterial infection in the subject. In still further embodiments, the determining comprises the detection of a viral infection in the subject.

The present invention also provides a method of screening compounds, comprising providing a sample from a subject, wherein the subject has undergone organ transplant; reagents for detection of a CXCR3 ligand or CCR-5 receptor ligand (e.g., CCL chemokines); and one or more test compounds; and administering the test compound to the subject; detecting the amount of the ligand in the sample using the reagents. The present invention is not limited to a particular sample type. Any bodily fluid including, but not limited to, blood, urine, serum, and lymph may be utilized. In some preferred embodiments, the sample is a urine sample. In some embodiments, the test compound is an anti-rejection drug. In some embodiments, the method further comprises the step of determining the efficacy of the anti-rejection drug based on the detecting. The present invention is not limited to the detection of a particular ligand. Any suitable ligand is contemplated including, but not limited to, IP-10, MIG, I-TAC, MIP-1α, MIP-3α, and MIP-1β. In some embodiments, the ligand is a full-length ligand. In other embodiments, the ligand is a fragment of a full-length ligand. In some embodiments, the reagents comprise reagents for performing an immunoassay. The present invention is not limited to a particular immunoassay. Any suitable immunoassay is contemplated including, but not limited to, ELISA, radioimmunoassay, automated immunoassay, and immunoprecipitation assay. In some embodiments, the ELISA is a quantitative ELISA assay. In some embodiments, the method further comprises the step of determining the presence or absence of a concurrent infection in the subject. In some embodiments, determining comprises determining the body temperature of the subject. In other embodiments, determining comprises the detection of a bacterial infection in the subject. In still further embodiments, determining comprises the detection of a viral infection in the subject.

In still further embodiments, the present invention provides a kit, comprising reagents for the detection of the amount of a CXCR3 ligand or CCR-5 receptor ligand (e.g., CCL chemokines) in a urine sample from a subject undergoing organ transplant, and instructions for using the reagents for detecting the presence of the ligand in the urine sample. The present invention is not limited to the detection of a particular ligand. Any suitable ligand is contemplated including, but not limited to, IP-10, MIG, I-TAC, MIP-1α, MIP-3α, and MIP-1β. In some embodiments, the reagents comprise reagents for performing an immunoassay. The present invention is not limited to reagents for a particular immunoassay. Reagents for any suitable immunoassay are contemplated including, but not limited to, ELISA, radioimmunoassay, automated immunoassay, and immunoprecipitation assay. In some embodiments, the ELISA is a quantitative ELISA assay. In some embodiments, the instructions comprise instructions required by the United States Food and Drug Administration for use in in vitro diagnostic products. In some embodiments, the kit further comprises second reagents for determining the presence or absence of a concurrent infection in the subject and second instructions for using the reagent for determining the presence of absence of the concurrent infection in the subject. In some embodiments, the second instructions comprise instructions for determining the body temperature of the subject. In other embodiments, the second reagents comprise reagents for the detection of a bacterial infection in the subject. In still further embodiments, the second reagents comprise reagents for the detection of a viral infection in the subject. In some embodiments, the instructions further comprise instructions for using the kit for diagnosing organ transplant rejection. In other embodiments, the instructions further comprise instructions for using the kit for predicting the risk of organ transplant rejection.

DEFINITIONS

Figure 1:
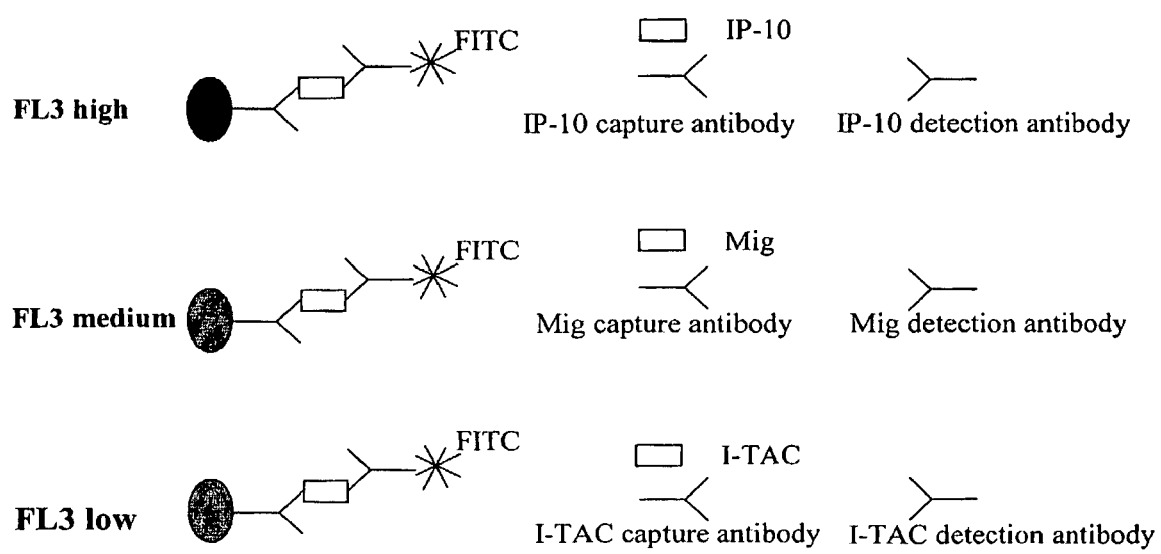
FIG. 1 shows an experiment design of the Beads FACS method for quantification of chemokines IP-10, Mig and I-TAC used in some embodiments of the present invention.

To facilitate an understanding of the present invention, a number of terms and phrases are defined below:

As used herein, the term "immunoglobulin" or "antibody" refer to proteins that bind a specific antigen. Immunoglobulins include, but are not limited to, polyclonal, monoclonal, chimeric, and humanized antibodies, Fab fragments, $F(ab')_2$ fragments, and includes immunoglobulins of the following classes: IgG, IgA, IgM, IgD, IbE, and secreted immunoglobulins (sIg). Immunoglobulins generally comprise two identical heavy chains and two light chains. However, the terms "antibody" and "immunoglobulin" also encompass single chain antibodies and two chain antibodies.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, $F(ab')_2$ fragments, and Fab expression libraries; and single chain antibodies.

The term "epitope" as used herein refers to that portion of an antigen that makes contact with a particular immunoglobulin.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular diagnostic test or treatment. Typically, the terms "subject" and "patient" are used interchangeably herein in reference to a human subject.

As used herein, the term "rejection polypeptide" refers to a polypeptide that, when present at elevated levels in a patient (e.g., in the urine of a patient), is indicative of organ transplant rejection or increased risk of organ transplant rejection. In some embodiments, rejection polypeptides are chemokines. In some preferred embodiments, the chemokines are CXCR3 chemokines, including, but not limited to, IP-10, MIG, and I-TAC. In other embodiments, the chemokines are CCL class chemokines, which bind to the CCR-5 receptor. Exemplary CCL class chemokines include, but are not limited to, MIP-1α, MIP-3α, and MIP-1β.

As used herein, the term "predicting kidney transplant rejection risk in a subject" refers to determining the risk of a subject rejecting a kidney transplant at any point following the transplant. In some embodiments, predicting kidney transplant rejection risk is based on "detecting the amount of a CXCR3 ligand in the urine of a subject" or "detecting the amount of a CCL chemokine in the urine of a subject." As used herein, the terms "detecting the amount of a CXCR3 ligand in the urine of a subject" and "detecting the amount of a CCL chemokines in the urine of a subject" refer to a quantitative or qualitative measure of the amount of a particular CXCR3 or CCL ligand in the urine of a subject. In some embodiments, the detecting utilizes "reagents for detection of a CXCR3 ligand" or "reagent for the detection of a CCL chemokines."

As used herein, the term "reagents for detection of a CXCR3 ligand" refers to reagents specific for the detection of a given CXCR3 ligand (e.g., IP-10, MIG, and I-TAC), for example, in urine of a subject. In some embodiments, the reagent is an antibody specific for the CXCR3 ligand. In some embodiments, the reagents further comprise additional reagents for performing detection assays, including, but not limited to, controls, buffers, etc.

As used herein, the term "reagents for detection of a CCL chemokine" refers to reagents specific for the detection of a given CCL chemokine (e.g., MIP-1α, MIP-3α, and MIP-1β), for example, in urine of a subject. In some embodiments, the reagent is an antibody specific for the CCL chemokine. In some embodiments, the reagents further comprise additional reagents for performing detection assays, including, but not limited to, controls, buffers, etc.

As used herein, the terms "instructions for using said kit for detecting kidney transplant rejection in said subject" and "instructions for using said kit for predicting kidney transplant rejection in said subject" include instructions for using the reagents contained in the kit for the detection and prediction of kidney transplant rejection in a sample from a subject. In some embodiments, the instructions further comprise the statement of intended use required by the U.S. Food and Drug Administration (FDA) in labeling in vitro diagnostic products. The FDA classifies in vitro diagnostics as medical devices and required that they be approved through the 510(k) procedure. Information required in an application under 510 (k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use, including photographs or engineering drawings, where applicable; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; and 8) Any additional information regarding the in vitro diagnostic product requested that is necessary for the FDA to make a substantial equivalency determination. Additional information is available at the Internet web page of the U.S. FDA.

As used herein, the term "determining a treatment course of action" as in "determining a treatment course of action based on said predicting kidney transplant rejection risk" or "determining a treatment course of action based on said diagnosing kidney transplant rejection," refers to the choice of treatment administered to a patient. For example, if a patient is found to be at increased risk of organ rejection or to be undergoing organ rejection, anti-rejection therapy may be started, increased, or changed from one treatment type (e.g., pharmaceutical agent) to another. Conversely, if a patient is found to be at low risk for organ rejection, anti-rejection therapy may not be administered or levels of anti-rejection therapy may be decreased. In some embodiments, the treatment course of action is "continued monitoring" in which no anti-rejection treatment is administered but the levels of rejection polypeptide in the patients urine is monitored regularly (e.g., using the diagnostic methods of the present invention).

As used herein, the term "determining the efficacy of said anti-rejection drug based on said detecting" refers to determining if a anti-rejection drug is preventing transplant rejection based on, for example, detecting the level of anti-rejection polypeptide in the urine of a patient who has undergone organ transplant.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., transplant rejection). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include urine and blood products, such as plasma, serum and the like. Such examples are not however to be construed as limiting the sample types applicable to the present invention.

DETAILED DESCRIPTION OF THE INVENTION

The present invention provides systems and methods for the diagnosis of organ transplant rejection. In particular, the present invention provides methods of predicting and diagnosing kidney transplant rejection based on the presence of rejection polypeptides in bodily fluids (e.g., urine). The present invention further provides methods of screening candidate anti-rejection drugs for their efficacy in preventing organ rejection.

The present invention provides a novel, non-invasive method of correlating the presence of certain chemokines in urine with transplant rejection. The methods are a significant improvement in terms of decreased cost and physical trauma to a patient. The methods of the present invention provide the further advantage of allowing home testing by patients.

I. Detection of Rejection Polypeptides in Urine

In some embodiments, the present invention provides methods of predicting and diagnosing transplant organ rejection by detecting rejection polypeptides in urine. The present invention is not limited to the detection of a particular rejection polypeptide or a particular detection assay. The below description provides non-limiting examples of suitable rejection polypeptides and detection methods. The present invention further provides kits for use in detecting rejection polypeptides in urine.

A. Rejection Polypeptides

The present invention provides methods of detecting rejection polypeptides in urine. The rejection polypeptides of the present invention are correlated with transplant organ rejection. In some embodiments, the presence of the peptides or an increased amount of the peptides is indicative of organ rejection. In other embodiments, increased rejection polypeptides are correlated with increased risk of transplant rejection. In preferred embodiments, the amount of rejection polypeptide is quantitated. In some preferred embodiments, a quantitative level of rejection polypeptide is determined that is indicative of an increased risk of organ rejection or ongoing organ rejection. In other embodiments, the level of rejection polypeptide is correlated with a functioning level of anti-rejection drug (e.g., the correct amount or a functional drug).

In some embodiments, rejection polypeptides are chemokines. In some preferred embodiments, the chemokines are CXCR3 chemokines. CXCR3 chemokines include, but are not limited to, IL-10, MIG, and I-TAC. In other embodiments, the chemokines are CCL chemokines. CCL chemokines bind to the CCR-5 receptor and include, but are not limited to, MIP-1$\alpha$, MIP-3$\alpha$, and MIP-1$\beta$.

The present invention is not limited to a particular rejection polypeptide. Any polypeptide that predicts ongoing organ rejection or the risk of future rejection may be utilized. Prospective polypeptides may be identified based on their correlation with individuals likely to reject an organ or who are rejecting an organ. Such information can be obtained from clinical studies of patients undergoing organ transplant. For example, in some embodiments, the level of a prospective rejection polypeptide in a subject's urine is measured prior to and post organ transplant. Patients are monitored for transplant rejection. Preferred polypeptides are those present at higher levels in the urine of patients that reject organs than in the urine of patients that do not reject organs.

The present invention is not limited to polypeptides associated with the rejection of a particular organ. It is contemplated that the methods of the present invention are suitable for monitoring rejection of a wide variety of transplanted organs. In some preferred embodiments, kidney rejection is monitored. Polypeptides described herein, as well as additional polypeptides, can be screened for their association with a particular organ transplant using the screening methods described herein.

In some embodiments, two or more (e.g., 3 or more, 4 or more, etc.) rejection markers are detected to provide a risk assessment. The presence of each marker may provide a more definitive answer than the analysis of any single marker alone. For example, as described in Example 2 below, detection of both IP-10 and I-TAC provided a 100% correlation to acute rejection in the patient group tested.

In some embodiments, certain threshold levels of a particular marker are detected. If the threshold level is reached, risk of objection is observed. For example, if 100 pg/ml of the rejection marker (e.g., IP-10, I-TAC) in urine is observed, risk is observed. The present invention is not limited by the threshold level used in the analysis. In some embodiments, the threshold level is 20 pg/ml or more, more preferably, 50 pg/ml or more, and most preferably 100 pg/ml or more although both higher and lower threshold values are contemplated, as are intervals between these values.

B. Detection Methods

The present invention provides methods for detecting the presence of rejection polypeptides in a urine sample. In some embodiments, full-length rejection polypeptide is detected. In other embodiments, a fragment or a portion of a rejection polypeptide is detected. In preferred embodiments, the present invention additionally provides methods of quantitating the amount of a rejection polypeptide in urine. The present invention is not limited to a particular detection assay. Exemplary detection assays are described herein.

In some embodiments, rejection polypeptides are detected by binding of an antibody specific for the protein (i.e., an immunoassay). The present invention is not limited to a particular antibody. Any antibody (e.g., monoclonal or polyclonal) that detects rejection polypeptides may be utilized. Exemplary methods for the generation of antibodies are described below.

Antibody binding is detected by techniques known in the art. For example, in some embodiments, antibody binding is detected using a suitable technique, including but not limited to, radioimmunoassay, ELISA (enzyme-linked immunosorbant assay), "sandwich" immunoassay, immunoradiometric assay, gel diffusion precipitation reaction, immunodiffusion assay, precipitation reaction, agglutination assay (e.g., gel agglutination assay, hemagglutination assay, etc.), complement fixation assay, immunofluorescence assay, protein A assay, and immunoelectrophoresis assay.

In some preferred embodiments, a quantitative ELISA assay is utilized (See e.g., U.S. Pat. Nos. 5,958,715, and 5,484,707, each of which is herein incorporated by reference). In some preferred embodiments, the quantitative ELISA is a competitive ELISA. In a competitive ELISA, the wells of a microtiter plate are first coated with a fusion protein comprising all or a fragment of the rejection polypeptide (e.g., a CXCR3 or CCL ligand). The sample to be tested is added to the plate along with an antibody that is specific for the rejection polypeptide. The rejection polypeptide in the urine sample competes for binding to the antibody with the immobilized peptide. The plate is washed and the antibody bound to the immobilized rejection polypeptide is then detected using any suitable method (e.g., a secondary antibody comprising a label or a group reactive with an enzymatic detection system). The amount of signal is inversely proportional to the amount of rejection polypeptide present in the urine sample (e.g., a high signal is indicative of low amounts of rejection polypeptide being present in the urine).

In some embodiments, an automated detection assay is utilized. Methods for the automation of immunoassays include, but are not limited to, those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a diagnosis and/or prognosis based on the level of rejection polypeptide in the urine is utilized. In other embodiments, the immunoassay described in U.S. Pat. Nos. 5,789,261, 5,599,677 and 5,672,480, each of which is herein incorporated by reference, is utilized.

In still other embodiments, a protein chip array assay is utilized for detection (See e.g., U.S. Pat. No. 6,197,599, herein incorporated by reference). In such an assay, proteins (e.g., antibodies specific for a rejection polypeptide) are immobilized on a solid support such as a chip. A urine sample suspected of containing the rejection polypeptide is passed over the solid support. Bound rejection polypeptides are then detected using any suitable method. In some embodiments, detection is via surface plasmon resonance (SPR) (See e.g., WO 90/05305, herein incorporated by reference). In SPR, a beam of light from a laser source is directed through a prism onto a biosensor consisting of a transparent substrate, usually glass, which has one external surface covered with a thin film of a noble metal, which in turn is covered with an organic film that interacts strongly with an analyte, such as a biological, biochemical or chemical substance. The organic film contains antibodies (e.g., specific for a rejection polypeptide of the present invention), which can bind with an analyte (e.g., rejection polypeptide) in a sample to cause an increased thickness, which shifts the SPR angle. By either monitoring the position of the SPR angle, or the reflectivity at a fixed angle near the SPR angle, the presence or absence of an analyte in the sample can be detected.

In other embodiments, The PROTEINCHIP (Ciphergen Biosystems, Fremont, Calif.) is utilized for detection. The PROTEINCHIP system uses SELDI (Surface-Enhanced Laser Desorption/Ionization) technology to perform the separation, detection and analysis of proteins at the femtomole level directly from biological samples (See e.g., U.S. Pat. No. 6,294,790 and U.S. Patent Application US20010014461A1, each of which is herein incorporated by reference. In the PROTEINCHIP technology, proteins of interest (e.g., rejection polypeptides) are captured on the PROTEINCHIP Array (e.g., via a bound antibody) directly from the original source material. The chip is washed to remove undesired materials and bound proteins are detected using SELDI.

In some embodiments, a cytometric bead array assay is used (Quantum Plex kit, Bangs Laboratories; Cytometric Bead Array kit, BD Biosciences). These systems allow for multiple analyte detection with small volume samples.

The present invention is not limited to the detection of rejection polypeptides in urine. Any bodily fluid that contains elevated levels of rejection polypeptide correlated with organ transplant rejection may be utilized, including, but not limited to, blood, serum, lymph, and saliva.

In some particularly preferred embodiments, a combination of several chemokines are detected simultaneously in urine samples. In some embodiments, the present invention provides a fluorescently activated cell sorting (FACS) FACS method for the simultaneous detection of multiple rejection polypeptides. In some embodiments, the method uses fluorescence dye labeled beads that can detect multiple (e.g., at least 3) chemokines in one assay. In one exemplary embodiment (Example 3), the assay was used to detect IP-10, I-TAC and Mig. Detection of these three chemokines was conducted in the same test tube simultaneously as depicted in FIG. 1. As the chemokine concentration increases, the mean fluorescence intensity for each group of beads increases. This correlation between the chemokine concentration and the mean fluorescence establishes the basis for this FACS quantitative method. A standard curve for each chemokine was constructed. These results demonstrate a quantitative assay for the simultaneous detection of multiple chemokines.

The present invention is further not limited to the direct detection of rejection polypeptides. The present invention contemplates the detection of correlated polypeptides or compounds (e.g., rejection polypeptide mRNA, metabolites, etc.). In still further embodiments, the present invention provides methods of detecting the interaction of rejection polypeptides with rejection polypeptide receptors (e.g., CXCR3 or CCR-5 receptors).

C. Detection of Concurrent Infection

In some embodiments, assays for the detection of rejection polypeptides are combined with assays for the detection of concurrent infections (e.g., bacterial or viral infections) that may generate false-positive results. For example, infection may cause elevated levels of chemokines. In some embodiments, the presence of infection is monitored along with the presence of chemokines.

In some embodiments, infection is monitored by the presence of diagnostic symptoms (e.g., including, but not limited to, elevated body temperature, swelling or redness, and pain). In other embodiments, infection is monitored by monitoring the presence of infectious organisms such a bacteria, virus, or fungus. In still further embodiments, infection is monitored by monitoring the presence of elevated chemokines that are associated with infection, but not graft rejection. In yet other embodiments, infection is monitored by an elevated white blood cell count in a subject.

D. Kits

In some embodiments, the present invention provides kits for the detection of rejection polypeptides. In some embodiments, the kits contain antibodies specific for rejection polypeptides, in addition to detection reagents and buffers. In some embodiments, the kits contain reagents and/or instructions for testing for concurrent infections. In preferred embodiments, the kits contain all of the components necessary to perform a detection assay, including all controls, directions for performing assays, and any necessary software for analysis and presentation of results.

In some embodiments, the kits contain an assay in a test strip format. In such embodiments, the detection reagent (e.g., antibody), as well as any control or secondary antibodies, are affixed to a solid support. In some embodiments, the solid support is a test strip suitable for dipping into a solution of urine (See e.g., U.S. Pat. Nos. 6,352,862, 6,319,676, 6,277, 650, 6,258,548, and 6,248,596, each of which is herein incorporated by reference).

In some embodiments, the kits are marketed as in vitro diagnostics. The marketing of such kits in the United States requires approval by the Food and Drug Administration (FDA). The FDA classifies in vitro diagnostic kits as medical devices. The 510(k) regulations specify categories for which information should be included.

II. Patient Care

The present invention further provides methods of providing test kits to patients in a variety of settings. The test kits of the present invention are suitable for use in both clinical and home testing settings. In preferred embodiments, test kits are approved for sale as in vitro diagnostics as described above.

A. Home Testing

In some embodiments, the present invention provides kits for home testing. In preferred embodiments, the kits are approved as in vitro diagnostics for home use under 510 (k) guidelines as described above. Patients may use home test kits to monitor organ rejection after a transplant. In some embodiments, test kits for home use are qualitative rather than quantitative. For example, in some embodiments, the test registers a positive result if urine levels of a CXCR3 or CCL ligand are above a predetermined level (e.g., above approximately 100 pg/mL) or increase over time. In other embodiments, the tests are quantitative (e.g., utilizing the quantitative methods described above).

For example, in some embodiments, patients who are not receiving anti-rejection drugs (e.g., because they were determined to be non-rejecters via testing prior to or post transplant) monitor urine levels of CXCR3 or CCL ligands. In preferred embodiments, patients conduct regular monitoring (e.g., from once a day to once a month or every several months) to screen for early signs or organ rejection. In preferred embodiments, patients whose urine level of a CXCR3 or CCL ligand is above a pre-determined level (or register a positive result in a quantitative assay) are instructed to seek medical advice.

In other embodiments, the test kits are utilized by patients at home to monitor the effectiveness of an anti-rejection drug. For example, in some embodiments, a patient who is taking an anti-rejection drug following organ transplant monitors levels of a CXCR3 and/or CCL ligand on a regular basis (e.g., from once a day to once a month or every several months). If a patient's level of a CXCR3 or CCL ligand is above a pre-determined level (or registers a positive result in a quantitative assay), it may be indicative of organ failure caused by lack of an effective level of an anti-rejection drug. Such patients are advised to schedule a follow up with a practitioner (e.g., to adjust the medication levels or switch to a different anti-rejection drug).

B. Clinical-Based Testing

In other embodiments, testing is performed in a clinical (e.g., hospital or clinic) setting. In such embodiments, testing is generally ordered and interpreted by a physician or other clinician. In some embodiments, testing is carried out by a lab technician (e.g., in an in-house or external clinical lab). In preferred embodiments, clinical testing utilizes a quantitative assay for detection of a CXCR3 or CCL ligand. In some embodiments, testing is utilized to determine the likelihood of organ rejection in a subject who is about to, or has just recently, undergone organ transplant. In other embodiments, testing is utilized to monitor organ rejection in a subject who has undergone organ rejection and is not on anti-rejection medication. In still further embodiments, testing is utilized to monitor the effectiveness of anti-rejection medication. In some embodiments, testing is utilized as a follow up to home testing by a patient (e.g., when a CXCR3 or CCL ligand level is elevated or the patient has other clinical symptoms of rejection).

Based on the result of the clinical testing, the appropriate intervention is taken (e.g., including, but not limited to, an increase or decrease in levels of drug anti-rejection therapy, initiation of anti-rejection therapy, termination of anti-rejection therapy, or continued monitoring).

C. Home collection/Clinic Testing

In still further embodiments, testing is provided by a clinical lab but in the absence of a physician's order or interpretation. For example, in some embodiments, the patient collects a urine specimen and transports the specimen to a clinical lab (e.g., by mail or in person). The clinical lab then reports the result to the patient. In other embodiments, the patient provides a sample at a clinical lab, the sample is analyzed, and the results are returned to the patient. The patient then decides, based on the level of CXCR3 or CCL ligand in the urine (or the presence or absence of a positive result in a qualitative assay) whether or not to contact a physician for follow up care.

III. Antibodies

The present invention provides isolated antibodies. In preferred embodiments, the present invention provides monoclonal antibodies that specifically bind to an isolated polypeptide comprised of at least five amino acid residues of a CXCR3 or CCL ligand. These antibodies find use in the diagnostic methods described herein. In other embodiments, commercially available antibodies are utilized (e.g., available from any suitable source including, but not limited to, R & D System, Minneapolis, Minn.).

An antibody against a protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a CXCR3 or CCL ligand). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against a CXCR3 or CCL ligand) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a CXCR3 or CCL ligand polypeptide (further including a gene having a nucleotide sequence partly altered) can be used as the immunogen. Further, fragments of the protein may be used. Fragments may be obtained by any methods including, but not limited to expressing a fragment of the gene, enzyinatic processing of the protein, chemical synthesis, and the like.

IV. Drug Screening

In some embodiments, the present invention provides drug-screening assays (e.g., to screen for anti-rejection drugs). The screening methods of the present invention utilize the detection of a CXCR3 ligand. For example, in some embodiments, the present invention provides methods of screening for compounds that alter (e.g. increase or decrease) the expression of CXCR3 or CCL ligand. In some embodiments, the level of a CXCR3 or CCL ligand is detected (e.g., using a method described herein) in a subject that has undergone organ transplant prior to and following administration of a candidate anti-rejection compound. The increased level of a CXCR3 or CCL ligand is indicative of a candidate compound that is not preventing rejection. Conversely, preferred candidate compounds are those that prevent the elevation of CXCR3 or CCL ligand levels.

In some embodiments, drug screening assays are performed in animals. Any suitable animal may be used including, but not limited to, baboons, rhesus or other monkeys, mice, or rats. Animals models of transplant rejection are generated (e.g., by performing kidney or other organ transplants on the animals or by the administration of compounds that trigger rejection) and the effect of candidate rejection drugs on the animals is measured. In preferred embodiments, transplant rejection in the animals is measured by detecting levels of rejection polypeptides in the urine of the animals. The level of rejection polypeptides may be detected using any suitable method, including, but not limited to, those disclosed herein.

EXPERIMENTAL

The following examples are provided in order to demonstrate and further illustrate certain preferred embodiments and aspects of the present invention and are not to be construed as limiting the scope thereof.

Example 1

Correlation of Urine IP-10 with Graft Rejection

This example describes the correlation of urine levels of IP-10 with kidney graft rejection in human subjects. Forty-five human subjects that had undergone kidney transplant were utilized. Urine IP-10 levels were measured repeatedly following organ transplant. IP-10 levels were measured using a quantitative colorimetric sandwich ELISA assay (R & D Systems, Minneapolis, Minn.). Subjects were divided into two groups, rejecters and non-rejecters, based on kidney biopsies. Biopsies were classified using Banff criteria (Solez et al., Kidney Int., 44:411 [1993]). All of the subjects were receiving anti-rejection therapy at the time of the study. Urine from ten normal (non-transplant) subjects was also tested.

In a majority of the non-rejecters, IP-10 levels remained at a constant, low level or decreased over time. In the rejecters, IP-10 levels remained at a constant, high level or increased over time. A urine level of IP-10 of greater than approximately 100 pg/mL was associated with organ rejection. There was no detectable IP-10 in any of the normal control samples. This Example demonstrates that IP-10 levels are correlated with kidney transplant rejection.

Experiments conducted during the development of the present invention also demonstrated a correlation between CCL chemokines and rejection. For example, correlations were observed for the CCL chemokines MIP-1α, MIP-3α, and MIP-1β.

Example 2

Correlation of Urinary Chemokines with Graft Rejection and Treatment

The example describes the correlation of urinary chemokines levels with graft rejection and treatment. Urinary samples were collected from healthy individuals, kidney transplant recipients with stable graft function, and recipients with acute rejection. All patients with acute rejection were hospitalized and received anti-rejection therapy. Urinary samples were centrifuged, and supernatant was aliquoted and stored at −80° C. These samples, after thawing, were evaluated by ELISA for the expression of MCP-1, IP-10, and I-TAC.

Elevated Expression of Chemokines in Urinary Samples from Patients with Acute Rejection As shown in Table 1, chemokines IP-10 and I-TAC were significantly increased in the urinary samples of patients with acute graft rejection and acute tubular injury, compared to healthy controls and kidney transplant patients with other pathologic changes. As presented in Table 2, if 100 pg/ml was used as the cut-off level and IP-10 and I-TAC were considered simultaneously, 80% of samples from patients with rejection and acute tubular injury were above this level, but less than 5% of the patients in the remaining groups were above this level. This result indicates that detection of IP-10 and I-TAC in the urinary samples reflects the acute rejection/acute tubular injury in the kidney grafts.

MCP-1 was also examined in the urinary samples. In the present series of samples (Table 1), urinary MCP-1 was increased in patients with acute rejection or acute tubular injury. However, the difference of MCP-1 levels between acute rejection/acute tubular injury and the remaining groups of patients was not significant.

Return of Urinary Chemokine Levels to Baseline after Resolution of Acute Rejection Urinary samples were collected daily from patients with biopsy-proven acute graft rejection until the rejection resolved. IP-10 and I-TAC were determined in these samples with ELISA. IP-10 and I-TAC were elevated at the time of diagnosis, but the levels decreased after anti-rejection therapy was started, and finally returned to the baseline. These results indicate that chemokine levels are useful parameters for monitoring the therapeutic response to anti-rejection therapies. In contrast, MCP-1 levels did not return to baseline in at least 50% of the patients with acute rejection following successful treatment.

This example indicates that IP-10 and I-TAC levels correlate with acute rejection processes in the kidney graft.

Example 3

Flow Cytometry Based Technique for Quantification of Chemokines

This example describes a FACS method for the simultaneous detection of multiple chemokines. The fluorescence activated cell sorting (FACS) method uses fluorescence dye labeled beads that can detect 3 chemokines in one assay. In this example, IP-10, I-TAC and Mig were detected. Detection of these three chemokines was conducted in the same test tube simultaneously as depicted in FIG. 1. As the chemokine concentration increases, the mean fluorescence intensity for each group of beads increases. This correlation between the chemokine concentration and the mean fluorescence establishes the basis for this FACS quantitative method. A standard curve for each chemokine was constructed. This example demonstrates that EP-10, Mig and I-TAC can be simultaneously detected in a urinary sample.

TABLE 1

Urinary Chemokine Levels in Patients with Kidney Transplant

|  | Healthy Controls (n = 10) | Others (non-acute/Chronic Rejection; n = 16) | Chronic Rejection (n = 7) | Acute Tubular Injury (n = 3) | Suspicious Acute Rejection (n = 7) | Acute Rejection (n = 10) Day 1/Day 2* |
|---|---|---|---|---|---|---|
| IP-10 (pg/ml) | 1 | 12 | 31 | 362 | 27.8 | 376/579 |
| I-TAC (pg/ml) | 1 | 21 | 13 | 75 | 44 | 94.2/168 |
| MCP-1 (pg/ml) | 269 | 641 | 1908 | 3226 | 528 | 2060/2473 |

*Day 1/Day 2 indicates the biopsy day/the day after the biopsy day.

TABLE 2

Patients with Urinary IP-10 and I-TAC Levels above 100 pg/ml

|  | Healthy Controls (n = 10) | Others (non-acute/Chronic Rejection; n = 16) | Chronic Rejection (n = 7) | Acute Tubular Injury (n = 3) | Suspicious Acute Rejection (n = 7) | Acute Rejection (n = 10) Day 1/Day* |
|---|---|---|---|---|---|---|
| IP-10 | 0 | 0 | 0 | 3 | 1 | 7/6 |
| I-TAC | 0 | 0 | 0 | 1 | 0 | 4/6 |
| IP-10 or I-TAC | 0 | 0 | 0 | 3 | 1 | 8/8 |

*Day 1/Day 2 indicates the biopsy day/the day after the biopsy day.

Example 4

Urinary Chemokine Assay using the Luminex Microsphere Platform

This Example describes the detection of IP-10, I-TAC, and Mig levels using a urine chemokines assay that uses the Luminex microsphere platform. The protocol used was as follows:

A 50 µl sample was added to wells of a 96 well plate (including std. Curve). Twenty five µl of luminex microsheres covalently coupled to capture antibody (for multiplex assays, bead were pooled together) was added. The beads were incubated in a dark at room temp for 60 minutes on rocking platform. Next, 25 µl of biotinylated detection antibody (for multiplex assays, antibodies were pooled) was added. The reaction was then incubated in a dark at room temp for 60 minutes on rocking platform. Twenty five µl of streptavidin: PE was added and the reaction was incubate in the dark at room temp for 30 minutes on a rocking platform. Finally, 25 µl of stop solution was added and the results were read in a Luminex 100 IS machine. The results demonstrated that the Luminex assay is able to accurately detect urine chemokines concentrations.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of detecting rejection markers to identify a risk of kidney transplant acute rejection, chronic rejection, or acute tubular injury, comprising:
    a) providing
        i) a urine sample from a subject, wherein said subject has undergone organ transplant;
        ii) reagents for detection of interferon-γ inducible protein 10 (IP-10); and
    b) detecting an amount of IP-10 above 20 pg/ml in said urine sample using said reagents to identify a risk of kidney transplant acute rejection, chronic rejection, or acute tubular injury.

2. The method of claim 1, wherein said reagents comprise reagents for performing an immunoassay.

3. The method of claim 1, wherein said immunoassay is selected from the group consisting of an ELISA, radio-immunoassay, automated immunoassay, cytometric bead assay, and immunoprecipitation assay.

4. The method of claim 1, wherein said reagents comprise reagents for performing a cytometric bead assay.

* * * * *